United States Patent
Scully et al.

(10) Patent No.: US 12,195,362 B2
(45) Date of Patent: Jan. 14, 2025

(54) PERIODIC UVC DOSING

(71) Applicant: Crystal IS, Inc., Green Island, NY (US)

(72) Inventors: Christopher Scully, Troy, NY (US); Amy Wilson Miller, Ballston Lake, NY (US); Richard M. Mariita, Green Island, NY (US); Leo J. Schowalter, Latham, NY (US)

(73) Assignee: Crystal IS, Inc., Green Island, NY (US)

( * ) Notice: Subject to any disclaimer, the term of this patent is extended or adjusted under 35 U.S.C. 154(b) by 288 days.

(21) Appl. No.: 17/002,348

(22) Filed: Aug. 25, 2020

(65) Prior Publication Data

US 2021/0061679 A1    Mar. 4, 2021

Related U.S. Application Data

(60) Provisional application No. 62/891,503, filed on Aug. 26, 2019.

(51) Int. Cl.
*C02F 1/32* (2023.01)
*A61L 2/10* (2006.01)

(52) U.S. Cl.
CPC ............... *C02F 1/325* (2013.01); *A61L 2/10* (2013.01); *C02F 2201/3222* (2013.01); *C02F 2303/04* (2013.01)

(58) Field of Classification Search
CPC .............. C02F 1/325; C02F 2201/3221; C02F 2303/04; C02F 2201/3222;

(Continued)

(56) References Cited

U.S. PATENT DOCUMENTS 5,543,039 A * 8/1996 Odegaard ............... C02F 3/085
                                                    261/95
6,579,495 B1 * 6/2003 Maiden ................... C02F 1/325
                                                    210/748.11

(Continued)

FOREIGN PATENT DOCUMENTS

CN      103025665 A      4/2013
CN      106677307 A  *   5/2017

(Continued)

OTHER PUBLICATIONS

Crystal IS, "The Case for UVC LEDs in Spectroscopic Instrumentation: UVC LEDs Pave the Way for the Development of More Cost Effective Instruments" <URL=http://www.cisuvc.com/content/documents/files/TheCaseforUVCLEDs.WP.singlepages.pdf> (last accessed Oct. 22, 2020).

(Continued)

*Primary Examiner* — Xiuyu Tai
(74) *Attorney, Agent, or Firm* — Nutter, McClennen & Fish, LLP

(57) ABSTRACT

A photoreactor for disinfecting water includes at least one wall defining a chamber configured to contain fluid. The reactor also includes an inlet through which water flows into the chamber, and an outlet through which water exits the chamber. The reactor also includes a UVC LED. The LED is configured to power on for an active duration, and power off for an inactive duration. The active duration and the inactive duration define a period. The reactor also includes a controller configured to set a duty cycle for the period, where the duty cycle is a ratio of the active duration to the period. The duty cycle is less than or equal to about 1:100.

19 Claims, 6 Drawing Sheets

(58) Field of Classification Search
CPC ........ C02F 2201/3228; C02F 2201/326; C02F 2209/008; C02F 2209/44; C02F 2307/06; C02F 2201/3227; C02F 2301/028; C02F 2201/328; C02F 2103/026; C02F 2307/10; C02F 2209/15; C02F 2209/006; C02F 2209/21; C02F 2209/08; C02F 2305/10; C02F 2209/20; C02F 2209/11; C02F 2209/36; A61L 2/10; H05K 1/0204; H05K 7/20272; H05K 1/181; H05K 2201/10106; B67D 3/0032; B67D 3/0038; B67D 3/0077; B67D 2210/00015; A23L 3/28

See application file for complete search history.

(56) References Cited

U.S. PATENT DOCUMENTS

| | | | |
|---|---|---|---|
| 2005/0103722 | A1 | 5/2005 | Freydina et al. |
| 2005/0139552 | A1* | 6/2005 | Forsberg ............ E03B 3/28 62/635 |
| 2014/0356229 | A1* | 12/2014 | Farren ............ A23L 3/28 250/492.1 |
| 2016/0278424 | A1* | 9/2016 | Liao ............ B67D 3/0077 |
| 2017/0280737 | A1* | 10/2017 | Liao ............ C02F 1/325 |
| 2018/0093904 | A1 | 4/2018 | Collins et al. |
| 2018/0179087 | A1* | 6/2018 | Tirén ............ C02F 1/325 |
| 2019/0016610 | A1 | 1/2019 | Hoehne |
| 2019/0062180 | A1* | 2/2019 | Taghipour ............ C02F 1/325 |
| 2020/0290893 | A1 | 9/2020 | Sieth et al. |

FOREIGN PATENT DOCUMENTS

| | | |
|---|---|---|
| KR | 100628705 B1 * | 10/2006 |
| NL | 1041426 A | 3/2016 |

OTHER PUBLICATIONS

Duckworth K, et al., "Advanced oxidation degradation kinetics as a function of ultraviolet LED duty cycle", Water Science & Technology | 71.9 | May 2015, <URI= https://www.researchgate.net/publication/276431691_Advanced_oxidation_degradation_kinetics_as_a_function_of_ultraviolet_LED duty cycle? (last accessed Oct. 22, 2020).

International Search Report and Written Opinion for International Application No. PCT/US20/47796, mailed on Feb. 3, 2021 (12 pages).

Wright, Maury, "Crystal IS delivers UV-C LEDs suitable for commercial use in water disinfection", Jan. 31, 2018 (Jan. 31, 2018), LEDs Magazine <URL=https://www.ledsmagazine.com/specialty-ssl/iartide/16701550/crystal-is-delivers-uvc-leds-suitable-for-commercial-use-in-water-disinfection> (last accessed Oct. 23, 2020).

Rayvio—"Study: Antibacterial efficacy of LARQ UV-C Pitcher against aqueous heterotrophic bacteria," Internal Report Dated Aug. 23, 2019 (Date of publication unknown. Accessed on Mar. 27, 2022 at https://res.cloudinary.com/larq/image/upload/v1646002825/assets/spa/pdf/LARQ_Pitcher-RayVio_UV_Testing_Report.pdf), 4 pages.

European Patent Office, Extended European Search Report for Application No. 20858108.2, dated Feb. 13, 2023, 7 pages.

* cited by examiner

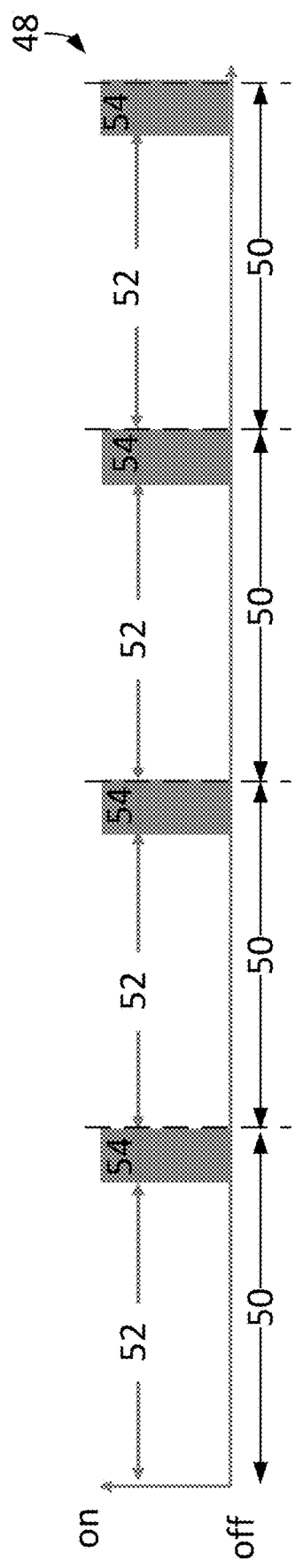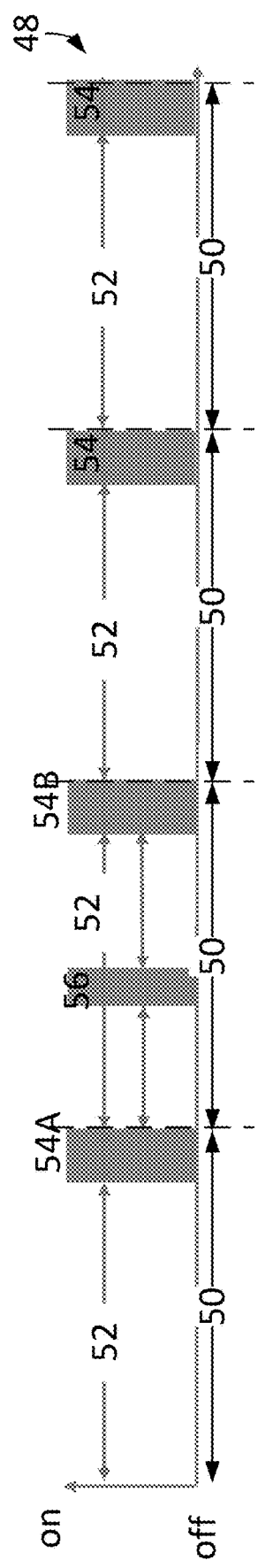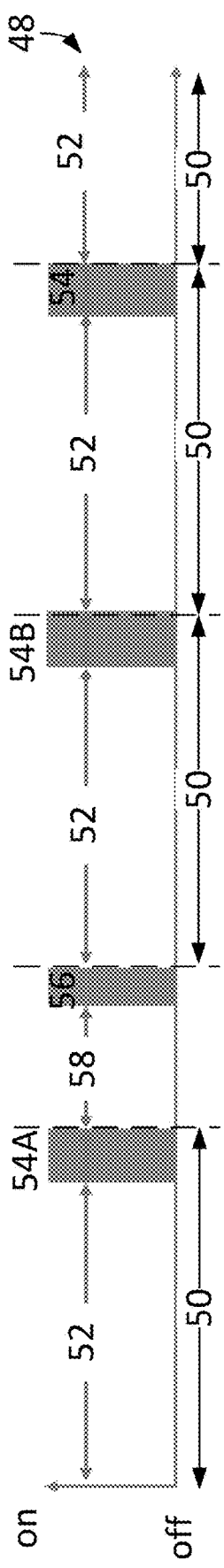

PERIODIC UVC DOSING

PRIORITY

This patent application claims priority from provisional U.S. patent application Ser. No. 62/891,503, filed Aug. 26, 2019, entitled, "PERIODIC UVC DOSING," and naming Christopher Scully, Amy Wilson Miller, Richard M. Mariita, and Leo J. Schowalter as inventors, the disclosure of which is incorporated herein, in its entirety, by reference.

FIELD OF THE INVENTION

Illustrative embodiments of the invention generally relate to treating drinking water by UV disinfection and, more particularly, illustrative embodiments relate to a UVC dosing schedule.

BACKGROUND OF THE INVENTION

With the exception of viruses, every cell of a living organism contains DNA, which allows the cell to function and reproduce. UV-C light penetrates the cells of microorganisms and disrupts the structure of their DNA molecules. This disruption prevents the microorganism from surviving and/or reproducing, rendering it inactive and no longer pathogenic.

SUMMARY OF VARIOUS EMBODIMENTS

In accordance with one embodiment of the invention, a photoreactor for disinfecting water includes at least one wall defining a chamber configured to contain fluid. The reactor also includes an inlet through which water flows into the chamber, and an outlet through which water exits the chamber. The reactor also includes a UVC LED. The LED is configured to power on for an active duration, and power off for an inactive duration. The active duration and the inactive duration define a period. The reactor also includes a controller configured to set a duty cycle for the period, where the duty cycle is a ratio of the active duration to the period. The duty cycle is less than or equal to about 1:100.

The duty cycle may be between about 1:100 and 1:5760. In various embodiments, the active duration may be between about 10 seconds and 5 minutes. The period may be between about 30 minutes and 48 hours.

The photoreactor may include a lidless LED. Additionally, the photoreactor may further include a cylinder within the chamber. The cylinder may be formed from UVC diffusively transmissive material and/or UVC diffusively reflective material.

In accordance with yet another embodiment a method periodically doses a UVC reactor. The method provides a photoreactor for disinfecting water. The photoreactor has at least one wall that defines a chamber configured to contain fluid. The photoreactor also has an inlet through which water flows into the chamber. The reactor also has an outlet through which water exits the chamber. Furthermore, the reactor has a UVC LED configured to be powered on for an active duration, and powered off for an inactive duration. The active duration and the inactive duration define a period. The method activates the UVC LED for a first active duration. The method also activates the UVC LED for a second active duration after a prescribed inactive duration.

Among other ways, the prescribed inactive duration may be determined based on the expiration of the first active duration. Alternatively, the prescribed inactive duration may be determined based on the expiration of a most recent LED activation. In various embodiments, a duty cycle is between about 1:60 and 1:2880. In some embodiments, the active duration (e.g., first active duration) occurs while the fluid in the reactor is stagnant (e.g., while the fluid does not flow through the reactor).

In accordance with another embodiment of the invention, a method of dosing UVC radiation within a reactor provides a fluid reactor. The fluid reactor has at least one UVC LED and a main photoreactor zone configured to house water. The main photoreactor zone is formed from material that is UVC diffusively reflective and UVC diffusively transmissive. The method also periodically doses the main photoreactor zone with UVC radiation using the at least one UVC LED. The UVC is dosed for a LED active duration. The periodic dosing is a function of an LED inactive duration. The LED may provide a dosage of UVC of greater than about 12.5 $mJ/cm^2$.

In some embodiments, respective LED active durations are the same temporal length. Additionally, respective LED inactive durations may be the same or different temporal lengths. In illustrative embodiments, the fluid is water. Advantageously, the periodical dosing may occurs as the water is stagnant. To that end, the periodic dosing may occur after a preset amount of time. However, in some embodiments, the preset amount of time may be reset by a trigger event, such as water flow and/or a remote request. To further reduce or eliminate bacterial growth, the method may also stir the water in the main photoreactor zone.

Illustrative embodiments of the invention are implemented as a computer program product having a computer usable medium with computer readable program code thereon. The computer readable code may be read and utilized by a computer system in accordance with conventional processes.

BRIEF DESCRIPTION OF THE DRAWINGS

Those skilled in the art should more fully appreciate advantages of various embodiments of the invention from the following "Description of Illustrative Embodiments," discussed with reference to the drawings summarized immediately below.

FIG. 6A schematically shows a periodic dosing protocol in accordance with illustrative embodiments of the invention.

FIG. 6B schematically shows a dosing schedule with periods based on expiration of the last scheduled UVC dose in accordance with illustrative embodiments of the invention.

FIG. 6C schematically shows an adjusted dosing schedule with periods based on expiration of the last UVC dose in accordance with illustrative embodiments of the invention.

DESCRIPTION OF ILLUSTRATIVE EMBODIMENTS

In illustrative embodiments, a water reactor includes one or more UVC LEDs (light-emitting diodes) that treat drinking water. The UVC LEDs are periodically activated ("dosed") to prevent and/or reduce bacterial growth. The periodic dosing includes times when the water is stagnant in the reactor. This is in contrast to methods that dose UV light continuously (e.g., mercury lamps) and undesirably generate large amount of heat, use relatively large amounts of power, and degrade the quality of the UV-system rapidly. This is also in contrast to methods that are only trigger activated, which may go long periods of time with untreated stagnant water. Details of illustrative embodiments are discussed below.

Figure 1:
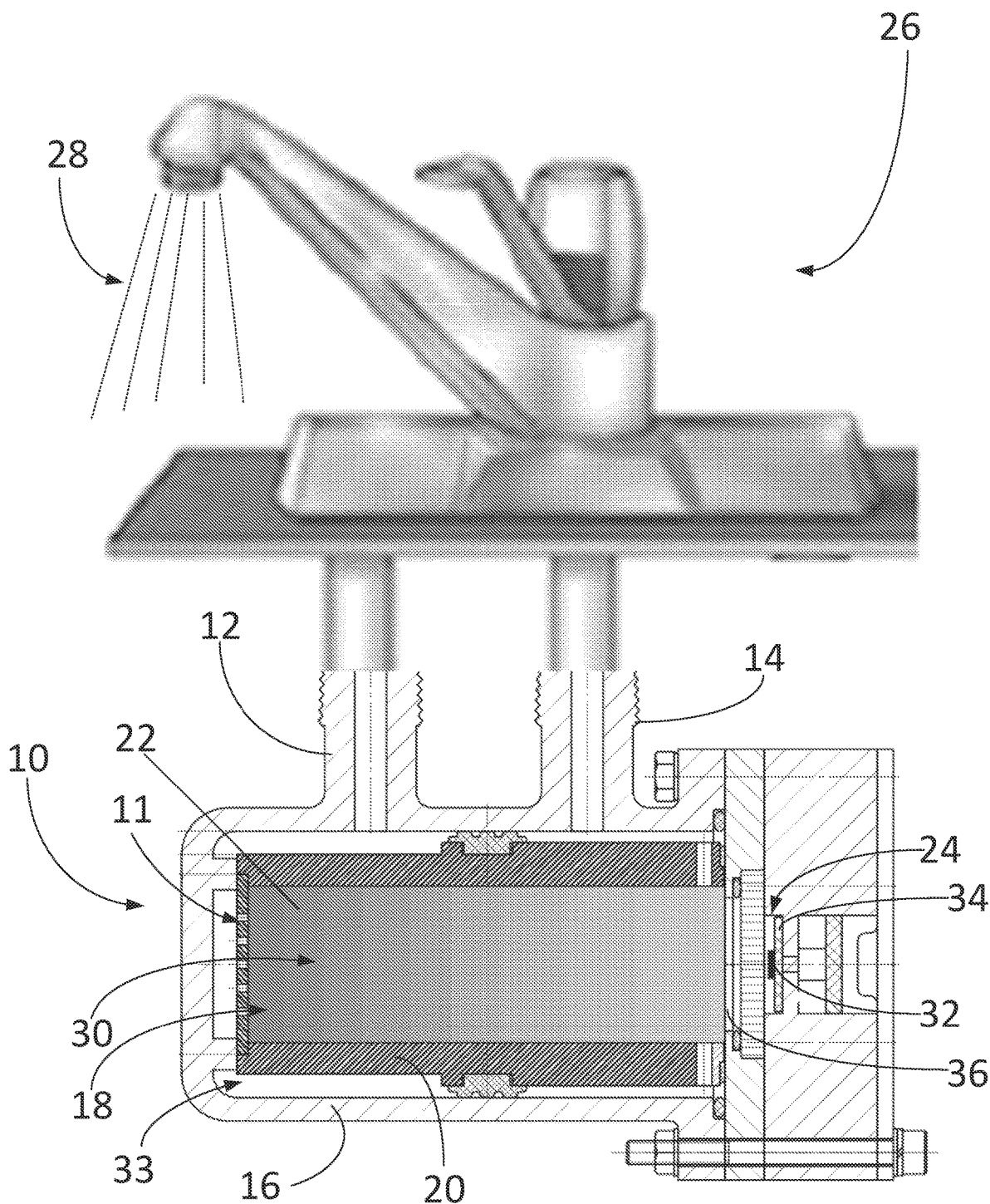
FIG. 1 schematically shows a UVC photoreactor in accordance with illustrative embodiments of the invention.

FIG. 1 schematically shows a UVC photoreactor 10 in accordance with illustrative embodiments of the invention. The UVC photoreactor 10 (also referred to as the reactor 10) may be coupled with, among other things, a fluid dispenser 26, such as a faucet 26 or a water cooler. Preferably, the reactor 10 is coupled with some source of drinking water, and disinfects the drinking water prior to consumption by a user.

As shown, the reactor 10 has an inlet 12 configured to receive fluid 22 from a source, such as water from a main water supply line. Although a variety of fluids 22 are contemplated with use herewith, for ease of discussion, water 22 is referenced throughout the description as the fluid 22. It should be understood however that illustrative embodiments may disinfect a variety of fluids.

To that end, the reactor 10 also includes at least one LED 24, preferably a UVC-emitting LED 24, that disinfects the fluid 22 in the chamber 18. The fluid 22 is disinfected and exits an outlet 14 of the reactor 10. For example, the outlet 14 may be coupled with a faucet 26 through which the user may obtain treated drinking water 28.

Although shown as directly coupled with the faucet 26, it should be understood that in various embodiments the reactor 10 may be directly or indirectly coupled with the fluid dispenser 26. Accordingly, illustrations are not intended to be considered limiting or to imply that a direct connection is necessary.

Like many reactors 10, the reactor 10 of FIG. 1 includes a wall 16 defining a chamber 18. The chamber 18 is configured to hold the water 22 therein. To better assist with disinfection, some embodiments may include a cylinder 20 formed from UVC transmissive and/or UVC reflective material, such as PTFE. For example, the cylinder may be formed from a material that is about 95% UVC reflective and about 5% UVC transmissive. The cylinder 20 may define a main photoreaction zone 30 and a peripheral photoreaction zone 33 within the chamber 18. The main photoreaction zone 30 may be surrounded by UVC diffusively transmissive and UVC diffusively reflective material (e.g., the material of the cylinder 20). Thus, the main photoreaction zone 30 may have a high-concentration of UVC light compared to the peripheral zone 33, which may have the cylinder 20 reflecting and/or absorbing at least a portion of UVC light emitted by the LED 24.

However, some other embodiments may form the cylinder 20 from, for example, a quartz tube. Preferably, illustrative embodiments of the cylinder 20, or portions thereof, are formed from a material that is both UVC diffusively reflective, and UVC diffusively transmissive (such as PTFE). For example, all of the surfaces of the cylinder 20 may be UVC diffusively transmissive and UVC diffusively reflective, and the wall 16 may be UVC reflective. In that way, UVC radiation scatters to irradiate a larger portion of surface area of the surfaces of the reactor 10, even outside of the main photoreaction zone 30.

Portions of the reactor 10 and/or the cylinder 20 may be formed from UVC transmissive material or UVC reflective material. For example, the UVC transmissive window 36 may be UVC diffusively transmissive. In some embodiments, the material used to form the reactor 10 (e.g., cylinder 20) may be partially transmissive to UVC. Additionally, or alternatively, the materials used to form the reactor 10 may be partially UVC reflective. Forming the reactor 10 using materials that are transmissive to UVC radiation allows the periodically dosed UVC to reach areas and surfaces that are susceptible to biofilm growth. Accordingly, illustrative embodiments may reduce and/or prevent the formation of biofilms through the reactor 10 (including outsize outside of the main photoreactor zone 30, also referred to as the main photoreaction zone 30).

Preferably, the wall 16 includes a UVC reflective material (as opposed to the a UVC absorbing material). Accordingly, the UVC radiation may be spread throughout the chamber 18 rather than isolated in a particular region/pocket. Additionally, forming the cylinder 20 from UVC transmissive material allows the UVC radiation to reach small pockets or regions either inside or outside the cylinder 20 that are not exposed (or only weakly exposed) to the UVC diffuse reflected radiation. Accordingly, UVC light may reach the peripheral zone 33.

In some embodiments, when the reactor 10 is in operation, the small pockets that are not exposed (or weakly exposed) generally do not form biofilms if the water 22 continuously circulates and is disinfected as soon as it moves through the pocket where there is no radiation (or the water is disinfected just before it goes through the "dark pocket"). However, when there is no water flow through the reactor 10, these dark pockets may support biofilm growth even when the chamber 18 is pulsed with radiation (e.g., because the radiation does not reach the dark pocket). By having at least part (or all) of the chamber 18 be formed from transmissive materials, illustrative embodiments ensure that no "dark pockets" exist and the radiation pulses reach all, or substantially all, parts of the chamber 18.

The reactor 10 may also include a diffuser plate 11. The diffuser plate 11 is configured to cause the water 22 to flow in a particular manner to assist with even dosing of UVC. Further discussion of the diffuser plate 11 is beyond the scope of this application. However, for the reasons described above, the diffuser plate 11 may also be formed from a material that is diffusively reflect and transmissive (such as PTFE).

The UVC LED 24 may be one or more of a variety of different types of LEDs 24. For example, the first type of LED 24 includes an LED chip 32, a package 34, and a lens (e.g., a quartz window) covering the LED chip 32 within the package. The second type of LED 24 includes an exposed LED chip 32 and a package 34 (e.g., a lidless package as shown in FIG. 1). The second type of LED 24 may be a commercially available device, such as the KLARAN™ UV LED, distributed by Crystal IS, Inc. and Asahi Kasei. With both LED 24 types, the reactor 10 may include a UV-transmissive material such as a quartz window 36 between the fluid chamber 18 and the LED 24. However, in some embodiments, the quartz window 36 may be removed, and an optical coupler may be positioned between the LED chip 32 and the chamber 18. The LEDs 10 and optical couplers are discussed in more detail in U.S. patent application Ser. No. 16/855,939, incorporated herein by reference in its entirety.

The UV LED chip 32, also referred to as the UV LED die 32, may be formed from a plurality of semiconductor layers (e.g., sapphire on GaAlN). A person of skill in the art understands that LED chip 32 may be formed of many more layers. In illustrative embodiments, the LED chip 32 is formed with an aluminum nitride (AlN) substrate having one or more quantum wells and/or strained layers, including AlN, gallium nitride (GaN), indium nitride (InN), or binary or tertiary alloy thereof. The LED chip 32 preferably has a substrate and/or device structure resembling those detailed in U.S. Pat. No. 7,638,346, filed on Aug. 14, 2006, U.S. Pat. No. 8,080,833, filed on Apr. 21, 2010, and/or U.S. Patent Application Publication No. 2014/0264263, filed on Mar. 13, 2014, the disclosures of which are incorporated herein, in their entireties, by reference. As known to those skilled in the art, the specific semiconductor materials and layer structure of the light emitting diode 24 may be selected so that a desired specific wavelength (or wavelength range) of light is emitted by the LED 24. In illustrative embodiments, the LED chip 32 emits UVC light. Preferred embodiments may have a peak wavelength in the UVC range. For example, the chip 32 may emit light having a peak wavelength of 260 nm to 270 nm to provide effective, consistent treatment of fluid.

For example, a small reactor 10 using a single 50 mW rated light emitting diode 24 with a 265 nm peak wavelength may produce a dose of approximately 40 mJ/cm$^2$ at a 0.5 liters per minute flow in a spherical reactor 10 with a chamber volume of only 0.3 cc (diameter of 0.8 cm) with an aperture (i.e., through which the LED 24 and/or chip 32 is positioned to emit light into the chamber) having an area of 1 mm$^2$. This favorably produces a six-log reduction in the pathogen of interest (*E. coli*), or approximately a four-log reduction in the QBeta phage, which is widely used as a surrogate for estimating the effectiveness of UV irradiation against other pathogens.

Figure 2:
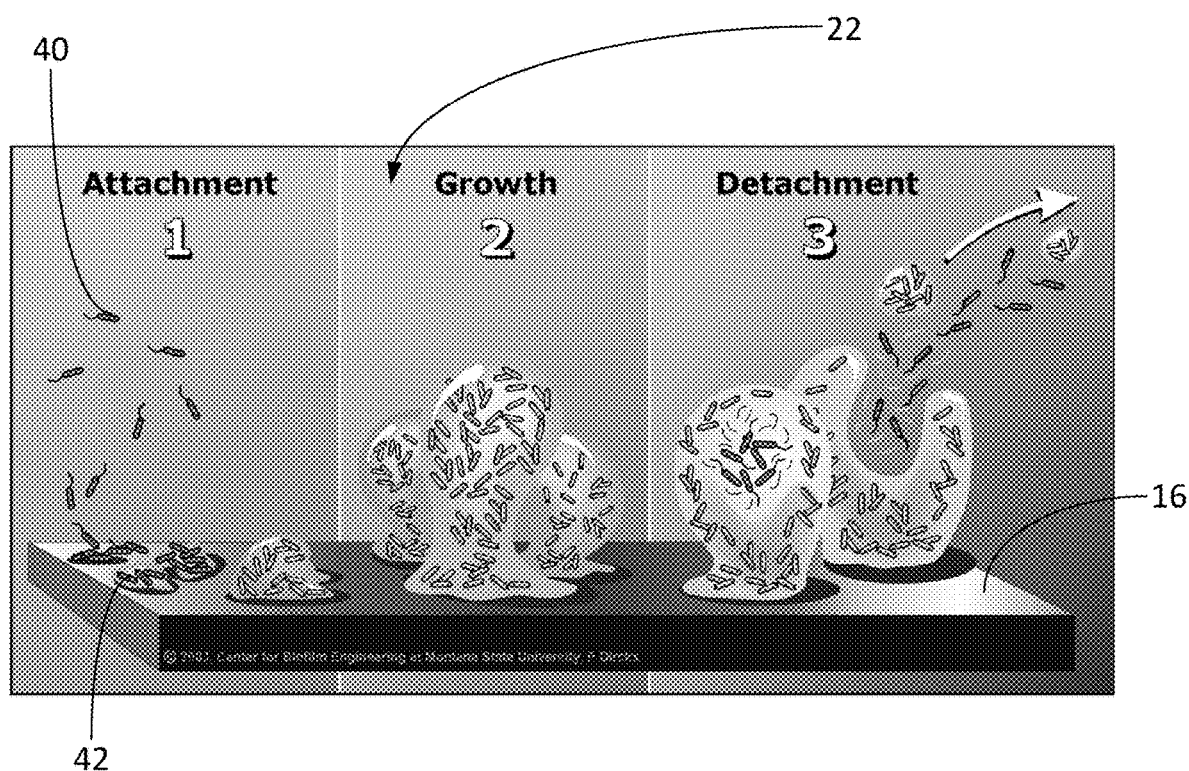
FIG. 2 schematically shows bacterial growth on a surface of the reactor in accordance with illustrative embodiments of the invention.

FIG. 2 schematically shows bacterial 40 growth on a surface of the reactor 10 in accordance with illustrative embodiments of the invention. The various surfaces of the reactor 10, such as the surfaces of the cylinder 20 and/or the wall 16, are subject to biofilm formation. Although surfaces of the reactor 10 are discussed, other surfaces inside and outside of the reactor 10 are also subject to growth.

Without wishing to be tied to any particular theory, it is believed that stagnant water (also referred to as static water) with any amount of both organic matter and living bacteria can form biofilms, or colonies 42 of bacteria 40 that may cling to surfaces 16 (schematically shown in attachment zone 1). The bacterial colonies 42 may then grow and proliferate on the surface 16 (schematically shown in growth zone 2). These surface colonies 42 may then act as vectors for spreading viable bacteria 40 into water 22 that flows across them (schematically shown in detachment zone 3). Accordingly, colonies 42 may grow upstream of the reactor 10 or even in the reactor 10 itself.

In various embodiments, the reactor 10 treats the water 22 by activating the LED 24 when a trigger event occurs. For example, the LED 24 may be activated when the faucet 26 is dispensing fluid. Thus, in theory, all (or substantially all) of the dispensed fluid 28 is treated as it travels through the reactor 10. The inventors discovered that use-based LED 24 treatment is sometimes insufficient to treat the various colonies 42 and/or bacteria 40 in the fluid 22. This is because use-based LED 24 treatment is subject to relatively long periods of non-use. For example, in a residential setting, users may go on vacation and therefore the LED 24 trigger event fails to occur at least for the length of the vacation period. In an office setting, the LED 24 trigger event fails to occur, for example, on the weekend when no one is in the office. Thus, the inventors recognized that a periodic passive system provides benefits of substantially reducing or eliminating bacterial 40 and/or colonies 42 that grow as a result of long periods of stagnation.

On the other hand, having prolonged periods without UVC dosing, such as with fluid flow triggered systems, may allow biofilms 42 to form. After the biofilm 42 has formed, it becomes difficult to remove and may continue to contaminate the water 22 with organisms even though the water 22 may be treated by UVC. Thus, bacterial 40 growth may occur and proliferate even where UV radiation is triggered by flow. Accordingly, some reactors 10 include a UVC mercury lamp, which is generally left on continuously.

The periodic UVC LED dosing of illustrative embodiments also offers numerous advantages over UVC mercury lamps. UVC mercury lamps are constantly left on to avoid the stresses of thermal cycling and/or to prevent degradation of the output power of the lamp. However, uninterrupted use of the lamp may waste energy and reduce the useful life of the system. In contrast, the LED 24 can be power cycled, and turned on and off instantly.

The inventors discovered that periodic dosing of UVC radiation prevents and/or reduces formation of biofilms. Furthermore, illustrative embodiments prevent and/or reduce bacterial 40 growth by using a microcontroller that controls the LED 24 to periodically transmits/radiate UVC light into the water 22 in the chamber 18. Accordingly, the bacteria 40 in the water 22 is dosed periodically (e.g., even when the water 22 is not flowing) and the bacterial 40 growth/biofilm formation is reduced and/or eliminated.

Figure 3:
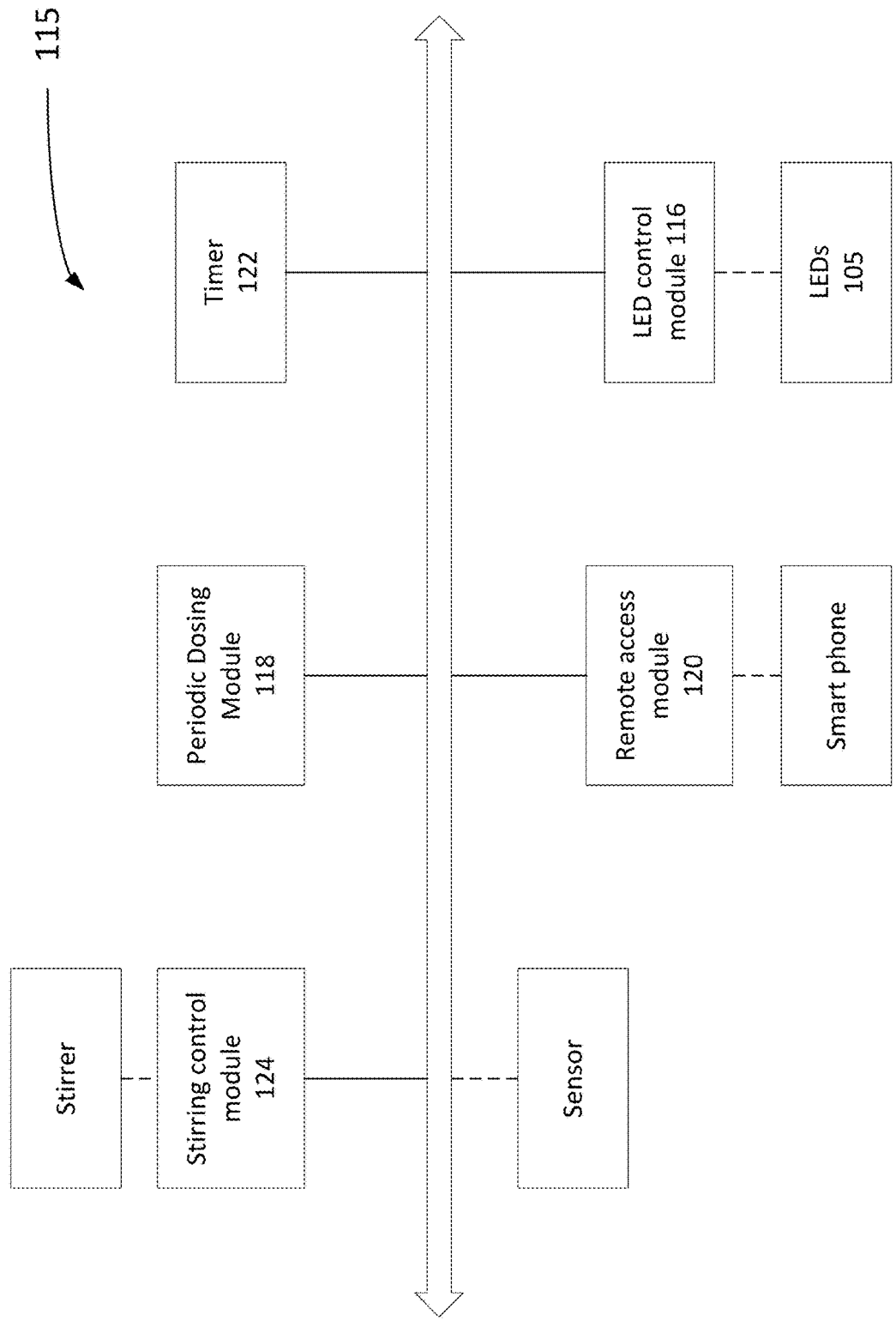
FIG. 3 shows details of a controller for controlling the LED in accordance with illustrative embodiments of the invention.

FIG. 3 shows details of a controller 115 for controlling the LED 24 in accordance with illustrative embodiments of the invention. In illustrative embodiments, the controller, such as a microcontroller 115, controls the operation of the LED 24. Specifically, the microcontroller 115 activates the LED 24, thereby causing the LED 24 to emit UVC radiation. Although the microcontroller 115 is described as controlling the LED 24, it should be understood that the microcontroller may control a plurality of LEDs 24.

The microcontroller 115 may have a number of modules that communicate with a number of physical components (shown connected using dashed lines). For example, the microcontroller 115 may have a remote access module 120 that communicates with a user (e.g., to provide for setting of the dosing schedule, stirring commands, LED 24 activation, and/or to provide data/statistics about the water reactor 10). To that end, the remote access module 120 may communicate with a user's end device, such as a network connected smart phone (e.g., internet, Wi-Fi, Bluetooth). The user may control, view, send, and receive data to and from the remote access module.

Additionally, the microcontroller 115 may have an LED control module 116. The LED control module 116 communicates with the LED 24, and sends a signal that turns the LED 24 on and/or off. For example, the LED control module 116 may receive an LED activation command from the user through the remote access module 120. Additionally, or alternatively, the LED control module 116 may communicate with a periodic dosing module 118 that provides an instruction to periodically dose the LED 24.

Figure 4:
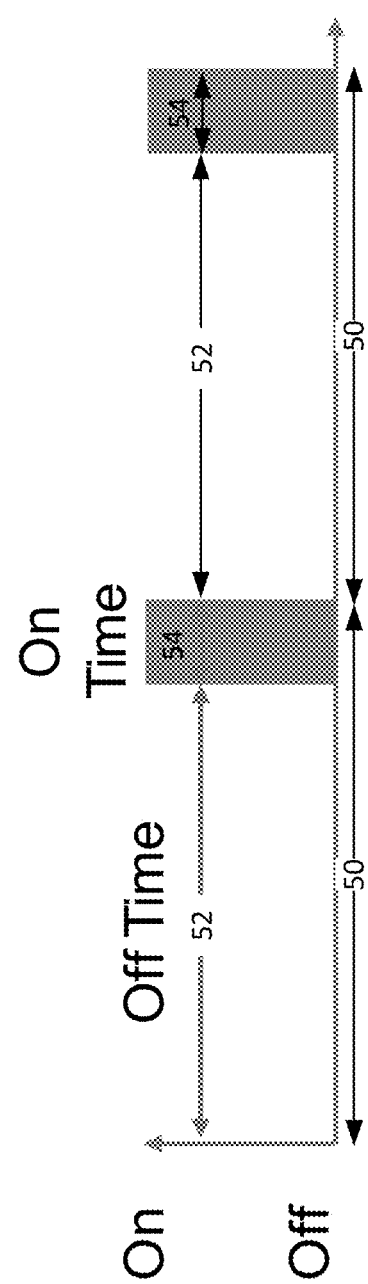
FIG. 4 schematically shows a periodic dosing protocol for the UVC LED in accordance with illustrative embodiments of the invention.

FIG. 4 schematically shows a periodic dosing protocol 48 for the UVC LED 24 in accordance with illustrative embodiments of the invention. The periodic dosing protocol 48 of FIG. 4 shows two full periods 50. Each period 50 includes a scheduled off-time 52, also referred to as an inactive duration 52, as well as a scheduled on-time 54, also referred to as an active duration 54. The periodic dosing module 118 provides instructions to the LED control module 116 to activate the LED 24 in accordance with a prescribed protocol 48. The protocol 48, which includes the active duration 54, the inactive duration 52, and/or the LED intensity, may be preset at the factory or adjusted by a user. For example, the user may adjust the periodic settings through the remote access module 120 described previously.

Additionally, or alternatively, the periodic dosing module 118 may adjust any aspect of the LED period 50 in real time based on feedback from one or more sensors. For example, the sensor may detect water flow, bacterial levels, and/or water volume, and adjust the period 50 automatically based on an underlying algorithm. The periodic dosing module 118 may further communicate with a timer 122 that allows the dosing module 118 to determine when the adequate inactive duration 52 has passed, so that the LEDs 24 may be turned on. Additionally, the timer 122 may determine when the active duration 54 has been achieved.

The microcontroller 115 may, in some embodiments, include a stirring control module 124 that controls a stirrer (not shown). The stirrer may be within the water reactor 10 (e.g., in the main photoreactor zone 30) and may continuously and/or periodically stir the water 22. The inventors believe that stirring the water 22 may assist with reducing bacterial 40 growth.

Each of the above-described components is operatively connected by any conventional interconnect mechanism. FIG. 3 simply shows a bus communicating each of the components. Those skilled in the art should understand that this generalized representation can be modified to include other conventional direct or indirect connections. Accordingly, discussion of a bus is not intended to limit various embodiments.

Indeed, it should be noted that FIG. 3 only schematically shows each of these components. Those skilled in the art should understand that each of these components can be implemented in a variety of conventional manners, such as by using hardware, software, or a combination of hardware and software, across one or more other functional components. For example, the periodic dosing module 118 may be implemented using a plurality of microprocessors executing firmware.

As another example, the LED control module 116 may be implemented using one or more application specific integrated circuits (i.e., "ASICs") and related software, or a combination of ASICs, discrete electronic components (e.g., transistors), and microprocessors. Accordingly, the representation of the components in a single box of FIG. 3 is for simplicity purposes only. In fact, in some embodiments, the LED control module 116 of FIG. 3 is distributed across a plurality of different machines—not necessarily within the same housing or chassis. Additionally, in some embodiments, components shown as separate (such as the timer 112 and the periodic dosing module 118) may be replaced by a single component. Furthermore, certain components and sub-components in FIG. 3 are optional. For example, some embodiments may not use the stirring control module 124 and/or the remote access module 120.

It should be reiterated that the representation of FIG. 3 is a significantly simplified representation of the water reactor 10 controller 115. Those skilled in the art should understand that such a device may have other physical and functional components, such as central processing units, other packet processing modules, and short-term memory. Accordingly, this discussion is not intended to suggest that FIG. 3 represents all of the elements of the water reactor 10 controller 115.

Figure 5:
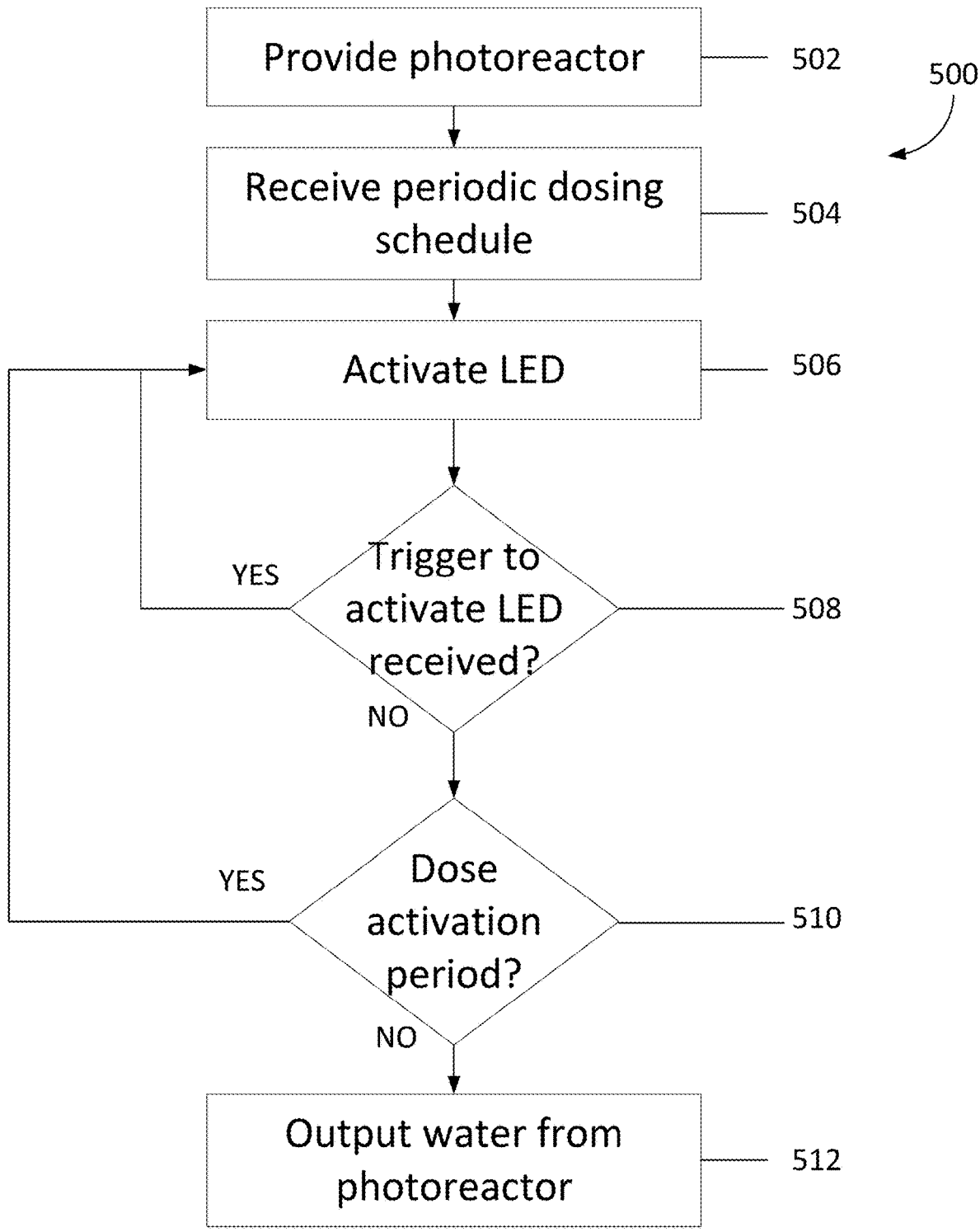
FIG. 5 shows a process of periodically dosing UVC in the water reactor in accordance with illustrative embodiments of the invention.

FIG. 5 shows a process of periodically dosing UVC in the water reactor 10 in accordance with illustrative embodiments of the invention. It should be noted that this process 500 can be a simplified version of a more complex process of periodically dosing UVC. As such, the process may have additional steps that are not discussed. In addition, some steps may be optional, performed in a different order, or in parallel with each other. Accordingly, discussion of this process is illustrative and not intended to limit various embodiments of the invention. Finally, although this process is discussed with regard to dosing a single LED 24 or a plurality of LEDs 24, the process of FIG. 5 can be expanded to alternatively cover a single LED 24 or including activating a plurality of LEDs 24 at the same time and/or alternating different times.

The process begins at step 502, which provides the photoreactor 10. The photoreactor 10 may be of the type shown in FIG. 1, and may have walls 16 and/or other surfaces on which bacterial colonies 42 may grow. It is contemplated that other microorganisms and deleterious pathogens beyond bacteria may be present in the water 22, but bacteria 40 is referenced for discussion purposes.

The photoreactor 10 may be present in a variety of settings. For example, the photoreactor 10 may be a mini-photoreactor, as described in U.S. patent application Ser. No. 16/855,939, incorporated herein by reference in its entirety. Alternatively, the photoreactor 10 may be part of a water purification system, e.g., as part of a water cooler in an office. There are a variety of use settings for the photoreactor 10 beyond those discussed here.

The process 500 proceeds to step 504, which receives a periodic dosing schedule. For example, the periodic dosing schedule may be preset in the periodic dosing module, and/or provided by a user (e.g., through the remote access module 120). FIG. 6A schematically shows a periodic dosing protocol 48 (also referred to as a dosing schedule 48) in accordance with illustrative embodiments of the invention. As shown, the schedule 48 includes a plurality of recurring periods 50. Although shown substantially identical, each of the periods 50 may differ. However, preferred embodiments have substantially identical periods 50.

As described previously each cycle has the active duration 54 and the inactive duration 52. The ratio of the active duration 54 relative to the period 50 is known as a duty cycle. Illustrative embodiments have a duty cycle (active duration 54:duration of period 50) of less than 1:60, for example, 1:100, 1:200, 1:400, 1:1440, 1:2880, or 1:5760. Here, "less than" or "smaller" duty cycle means that the active duration 54 is shorter relative to the period 50. The relatively small duty cycle provides many of the advantages previously described regarding energy savings. Additionally, the LED 24 can instantly power on and off, allowing for short active durations 54.

In illustrative embodiments, the lower limit for fluid treatment is approximately 10 seconds every 12 hours (e.g., duty cycle of 1:4348). Additionally, in illustrative embodiments, the upper limit may be around 2 minutes every hour (e.g., duty cycle of 1:30).

In some embodiments the active duration 54 may be greater than about 1 second, about 30 seconds, about 1 minute, or about 5 minutes. The active duration 54 may also be less than about 5 minutes, or about 10 minutes. The time of the period 50 may be between about 30 minutes and about 48 hours. Preferably, the period 50 is less than about 24 hours, to reduce the likelihood that colonies 42 have time to attach to a surface and begin to proliferate. Additionally, in some embodiments the period 50 is greater than about 1 hour, to provide reduced power usage.

The process then proceeds to step 506, which activates the LED 24. As mentioned earlier, one or more LEDs 24 may be activated. For simplicity, a single LED 24 is discussed here. The LED 24 may be pulsed as a single impulse (e.g., instantaneously power on and then off). However, it is contemplated that for the level of UVC radiation required to disinfect the various pathogens in the water 22, that the LED 24 is dosed for some duration 10. In some embodiments, a plurality of LEDs 24 may be activated each period 50. Some other embodiments may alternate to a different LED 24 for each period 50.

In some embodiments, the LED 24 may be constantly powered on. However, constant powering of the LED 24 may lead to degradation of quality of UVC radiation, unnecessary power expenditure, and thermal management problems. When the LED 24 emits UV light, it can produce a considerable amount of heat. Undesirably, excess heat negatively impacts the light output and lifetime of the LED 24. Thus, proper thermal management preferably keeps the junction temperature (TJ) as low as is required for the given application and maintains the performance of the LED. The word "junction" refers to the p-n junction within the LED 24 die, where the photons are generated and emitted. Heat may be transferred away from this junction to the ambient by coupling a heat sink with the LED 24. To further assist with heat transfer, illustrative embodiments preferably dose the LED 24 in periods 50 (e.g., as describe with reference to FIG. 4).

The process then proceeds to step 508, which determines whether there has been a trigger to activate the LED 24. As described here, the trigger does not include the normally scheduled activation period 54 of the periodic dosing schedule 48. In various embodiments, the trigger may include flow of fluid 22 through the reactor 10. For example, in the office setting, every time that drinking water 22 is dispensed, the LED 24 may be triggered. If the trigger is engaged, the process returns to step 506, which activates the LED 24.

Alternatively, the LED 24 may be triggered by the user through their smartphone (e.g., by sending a signal through the remote access module 120). Additionally, or alternatively, a sensor (e.g., in-line with the photoreactor 10) may determine that pathogens levels has reached a particular trigger threshold, and trigger activation of the LED 24.

In some embodiments, if water 22 is flowing, or if a request has been made (e.g., by a user over a network connected device), the process proceeds to step 506, which doses the LEDs 24. Accordingly, the LED control module 116 sends a signal to one or more of the LEDs 24 that causes them to transmit UVC radiation into the photoreactor 10 (e.g., into the main photoreactor zone 30). As mentioned previously, flow of water 22 may act as a trigger for activation of the LEDs 24. The LEDs 24 may have an active duration 10 that lasts for the entire period that water 22 is flowing, or alternatively, may have a set activation duration 10 upon detection of the flow trigger (e.g., activate LEDs 24 for 10 seconds from onset of flow regardless of amount of time that flow lasts). The process then returns to step 502 and begins again.

The process then proceeds to step 510, which determines whether the periodic dosing module 118 has requested a dose of UVC (i.e., based on the dosing schedule 48). If the periodic dosing module 118 has requested a dose, then the LED control module 116 activates the LEDs 24 for the prescribed amount duration 54.

In some embodiments, the periodic dosing may include a more complex period 50 (e.g., 2-minute activation duration 54 at the 12-hour mark, 1-minute activation duration 54 at the 24-hour mark). However, in some other embodiments, the dosing schedule 48 may be irregular or triggered by some other event (e.g., bacterial colony 42 cell count in water 22 surpasses a trigger level).

If the periodic dosing module 118 requests a dose, then the LED 24 is activated for the length of the activation duration 54. The length of the LED activation duration 54 may be predetermined and set by the microcontroller 115. For example, the periodic dosing module 118 may wait for the scheduled off-time 52 before sending a signal to the LED control module 116 to begin the LED activation duration 54. To that end, the periodic dosing module 118 may communicate with a timer 122 to accurately determine when to begin the activation duration 54. After the expiration of the activation duration, the timer 122 begins counting the amount of time since the LED 24 was last dosed.

Thus, the off-time 52 until the onset of the next active duration 54 is determined based on the time the LED 24 was last dosed. However, some embodiments determine the off-time 52 based on the expiration of the scheduled active duration 54.

FIG. 6B schematically shows a dosing schedule 48 with periods 50 based on expiration of the last scheduled UVC dose in accordance with illustrative embodiments of the invention. Thus, if the trigger is detected, and the LED 24 is trigger activated 56 outside of the dosing schedule 48 (e.g., by a user running the faucet 26), the next scheduled active duration 54B is based off the expiration of the previously scheduled active duration 54A. Thus, some embodiments maintain the scheduled period 50 regardless of how often the LED 24 is activated.

FIG. 6C schematically shows an adjusted dosing schedule 48B with periods 50 based on expiration of the last UVC dose in accordance with illustrative embodiments of the invention. Thus, if the LED 24 is trigger activated 56 outside of the dosing schedule 48 (e.g., by a user running the faucet 26), the next scheduled active duration 54B is based off the expiration of the most recent LED activation 56 (i.e., even if it is unscheduled). Accordingly, some embodiments restart the period 50 based on the most recent LED 24 activation.

As shown, the active duration 54 may occur at regular intervals. For example, the active duration 54 may be initiated for 2-minutes of a 12 hour period 50. This may occur on a repeated basis. Thus, another active duration 54 that lasts for 2-minutes occurs at the 12-hour mark, and then again at the 24-hour mark. In such embodiments, the duty cycle is less than 1% (i.e., duty cycle of less than 1:100 (active duration 54:total time per cycle 50)). Indeed, in the above described example, the duty cycle is less than 0.5%. The small duty cycle results in treatment of the water 22 (e.g., disinfection), considerable power savings, and greatly extends the useful life of the LED 24.

The periodic dosing module 118 may request a dose based on the preset timer 122. For example, as shown in FIG. 6A, the dose may automatically be requested automatically after some inactive period 52. Thus, in some embodiments, the dose may be delivered (active duration 54) automatically after a preset amount of time. However, in some other embodiments, the inactivate period 52 may be adjusted based on, e.g., the period of time since the LED 24 was activated through water flow or remote request, the volume of water within the reactor, and/or the amplitude of the output power of the LEDs 24.

In a similar manner, the LED active duration 54 may automatically begin after each inactive period 54. As described previously, the temporal length of the active duration 54 may be preset by the microcontroller 115. In some embodiments, the active duration 54 may be the same length for repeated doses. However, in some other embodiments, the activation period 10 may be adjusted, for example, based on the volume of water 22 within the reactor 10, the period of time since the LED 24 was activated through water 22 flow or remote request, the volume of water 22 within the reactor 10, and/or the amplitude of the output power of the LEDs 24. Thus, as an example, the activation period may be shorter for a stronger dose of UVC or longer for a weaker dose of UVC.

In some embodiments, the water reactor 10 may include the stirrer configured to cause the water 22 in the reactor 10 to move. While the water is moved during stirring, it is not considered to "flow" (e.g., in the way that the water 22 flows as it moves through the reactor—such as through a cooler to an end user's cup). Thus, in some embodiments, stirring the water 22 may affect the periodic dosing schedule. However, in some other embodiments, stirring the water 22 may not affect the periodic dosing schedule. Furthermore, in some embodiments the stirrer may periodically stir the water 22. In some other embodiments, the stirrer may continuously stir the water 22. The inventors discovered that stirring the water 22 eliminates some of the clinging biofilm 102 that may otherwise be formed.

In some embodiments, the periodic dosing schedule may be set to activate the LEDs 24 for 2 minutes (e.g., continuously) every 12 hours. As another example, the LEDs 24 may be active for 1 minute (e.g., continuously) every 6 hours. In some embodiments, the LEDs 24 may provide a dosage of, for example, 5 mJ/cm$^2$, for example, for 50 second active duration 54. In some other embodiments, the LEDs 24 may provide a dosage of 12.5 mJ/cm$^2$ for 125 second active duration 54. In various embodiments, dosages of between about 5 mJ/cm$^2$ and about 12.5 mJ/cm$^2$ may be provided during the active period 54 for about 10 seconds to about 10 minutes.

Returning to FIG. 5, if the periodic dosing module 118 has not requested a dose, then the process proceeds to step 512, and treated water 28 is output from the reactor. The user may then consume the treated water 28. The process 500 then comes to an end.

Illustrative embodiments dose UVC to reduce and/or prevent prokaryotic (lower unicellular organisms) microfouling, such as from different bacteria phyla, generally found in drinking water systems. In contrast, UVC dosing for marine antifouling has an application in preventing eukaryotic (higher multicellular organisms) macrofouling such as from barnacles, oysters, mussels and tube worms in open and marine water column systems, mostly vital in shipping and general boating industries (e.g., possibly via prevention of settlement of eukaryotic larvae).

Prokaryotic biofilm formation (microfouling) in drinking water systems is a fast process (relative to macrofouling) and occurs mostly in dark enclosed systems such as pipes, coolers, reactors, especially when water is stagnant. This is in contrast to macrofouling, which happens in more complex (a lot biotic and abiotic factors), but open environments impacted by waves, tidal changes (low and high tide), plus other marine physiochemical parameters.

Various embodiments of the invention may be implemented at least in part in any conventional computer programming language. For example, some embodiments may be implemented in a procedural programming language (e.g., "C"), or in an object oriented programming language (e.g., "C++"). Other embodiments of the invention may be implemented as preprogrammed hardware elements (e.g., application specific integrated circuits, FPGAs, and digital signal processors), or other related components.

In an alternative embodiment, the disclosed apparatus and methods (e.g., see the various flow charts described above) may be implemented as a computer program product for use with a computer system. Such implementation may include a series of computer instructions fixed either on a tangible, non-transitory medium, such as a computer readable medium (e.g., a diskette, CD-ROM, ROM, or fixed disk). The series of computer instructions can embody all or part of the functionality previously described herein with respect to the system.

Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies.

Among other ways, such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). In fact, some embodiments may be implemented in a software-as-a-service model ("SAAS") or cloud computing model. Of course, some embodiments of the invention may be implemented as a combination of both software (e.g., a computer program product) and hardware. Still other embodiments of the invention are implemented as entirely hardware, or entirely software.

Disclosed embodiments, or portions thereof, may be combined in ways not listed above and/or not explicitly claimed. In addition, embodiments disclosed herein may be suitably practiced, absent any element that is not specifically disclosed herein. Accordingly, the invention should not be viewed as being limited to the disclosed embodiments.

The embodiments of the invention described above are intended to be merely exemplary; numerous variations and modifications will be apparent to those skilled in the art. Such variations and modifications are intended to be within the scope of the present invention as defined by any of the appended claims.

What is claimed is:

1. A method of periodically dosing a UVC reactor, the method comprising:

providing a photoreactor for disinfecting fluid, the photoreactor having:
at least one wall defining a chamber configured to contain the fluid,
an inlet through which the fluid flows into the chamber,
an outlet through which the fluid exits the chamber, and
a UVC LED configured to be powered on for an active duration, and powered off for a prescribed inactive duration, the active duration and the prescribed inactive duration defining a period, wherein the period is between about 6 hours and about 24 hours;

activating the UVC LED for a first active duration of between about 10 seconds and about 5 minutes;

activating the UVC LED for a second active duration after the prescribed inactive duration.

2. The method as defined by claim 1, wherein the prescribed inactive duration is determined based on expiration of the first active duration or the prescribed inactive duration is determined based on the expiration of a most recent LED activation.

3. The method as defined by claim 1, wherein the first active duration occurs while the fluid is stagnant.

4. The method as defined by claim 1, wherein a duty cycle is between about 1:72 and about 1:2880.

5. The method as defined by claim 1, wherein the UVC LED is a lidless type LED.

6. The method as defined by claim 1, wherein the photodetector further comprises a cylinder within the chamber, the cylinder formed from UVC diffusively transmissive material and/or UVC diffusively reflective material.

7. A method of dosing UVC radiation within a fluid reactor, the method comprising:

providing the fluid reactor having at least one UVC LED and a main photoreactor zone, the at least one UVC LED positioned so as to emit UVC light into the main photoreactor zone through a UVC transmissive window, the main photoreactor zone having a main photoreactor zone housing configured to house fluid, the main photoreactor zone housing being formed from material that is UVC diffusively reflective and UVC transmissive; and periodically dosing the main photoreactor zone with UVC radiation using the at least one UVC LED for a LED active duration as a function of an LED inactive duration that is reset when the at least one UVC LED emits radiation.

8. The method as defined by claim 7, wherein the fluid reactor has a peripheral photoreactor zone between the main photoreactor zone housing and a wall of the fluid reactor, the wall of the fluid reactor being UVC reflective, wherein the fluid reactor is configured so that the main photoreactor zone receives a greater concentration of UV light than the peripheral photoreactor zone, the main photoreactor zone further configured to house a larger volume of fluid than the peripheral photoreactor zone.

9. The method as defined by claim 7, wherein the respective LED inactive durations are different temporal lengths.

10. The method as defined by claim 7, wherein the periodically dosing occurs as the fluid is stagnant.

11. The method as defined by claim 7, wherein periodically dosing occurs after a preset amount of time.

12. The method as defined by claim 11, wherein the preset amount of time is reset by a trigger event.

13. The method as defined by claim 12, wherein the trigger event is fluid flow.

14. The method as defined by claim 12, wherein the trigger event is a remote request.

15. The method as defined by claim 7, further comprising periodically stirring the fluid in the main photoreactor zone.

16. The method as defined by claim 7, further comprising continuously stirring the fluid in the main photoreactor zone.

17. The method as defined by claim 1, further comprising:

configuring a controller to set a duty cycle for the period, wherein the duty cycle is a ratio of the active duration to the period, wherein the duty cycle is less than or equal to about 1:100.

18. The method as defined by claim 17, wherein the duty cycle is between about 1:100 and about 1:5760.

19. The method as defined by claim 7, wherein a period is between about 30 minutes and about 48 hours.

* * * * *